(12) United States Patent
Feith et al.

(10) Patent No.: US 10,767,774 B2
(45) Date of Patent: Sep. 8, 2020

(54) DUAL CHECK VALVE

(71) Applicant: CareFusion 303, Inc., San Diego, CA (US)

(72) Inventors: Raymond Feith, Chino Hills, CA (US); George Mansour, Diamond Bar, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 16/138,799

(22) Filed: Sep. 21, 2018

(65) Prior Publication Data

US 2019/0093775 A1 Mar. 28, 2019

Related U.S. Application Data

(60) Provisional application No. 62/562,347, filed on Sep. 22, 2017.

(51) Int. Cl.
*F16K 15/14* (2006.01)
*A61M 39/24* (2006.01)

(52) U.S. Cl.
CPC .......... *F16K 15/148* (2013.01); *A61M 39/24* (2013.01)

(58) Field of Classification Search
CPC ............................. F16K 15/148; A61M 39/24
USPC ................ 137/512.4, 512.15, 843, 854, 855
See application file for complete search history.

(56) References Cited

U.S. PATENT DOCUMENTS

| | | | |
|---|---|---|---|
| 4,729,401 A | 3/1988 | Raines | |
| 6,089,260 A | 7/2000 | Jaworski et al. | |
| 6,273,124 B1 | 8/2001 | Huber et al. | |
| 7,331,360 B2 * | 2/2008 | Camis, Jr. ............. | F16K 15/144 137/512.3 |

OTHER PUBLICATIONS

International Preliminary Report on Patentability from the International Preliminary Examining Authority for Application No. PCT/US2018/052243, dated Oct. 15, 2019, 19 pages.
Canadian Office Action for Application No. 3075286, dated Apr. 14, 2020, 4 pages.
International Search Report and Written Opinion for Application No. PCT/US2018/052243, dated Dec. 17, 2018, 11 pages.
Australian Office Action for Application No. 2018338315, dated Mar. 27, 2020, 4 pages.

* cited by examiner

*Primary Examiner* — P. Macade Nichols
(74) *Attorney, Agent, or Firm* — Morgan, Lewis & Bockius LLP

(57) ABSTRACT

A dual check valve includes an upper housing, an intermediate housing, and a lower housing, and a first valve seat. The intermediate housing is coupled to the upper housing to define a first cavity, and includes a second valve seat. The lower housing is coupled to the intermediate housing to define a second cavity. A first disk is mounted in the first cavity and configured to selectively contact the first valve seat. A second disk is mounted in the second cavity and configured to selectively contact the second valve seat. When the dual check valve is in an open state, the first disk deflects away from the first valve seat to create a first gap, and the second disk deflects away from the second valve seat to create a second. The first gap is smaller than the second gap.

20 Claims, 5 Drawing Sheets

DUAL CHECK VALVE

CROSS-REFERENCE TO RELATED APPLICATIONS

This application claims priority under 35 U.S.C. § 119 to Provisional Application No. 62/562,347 filed on Sep. 22, 2017, in the United States Patent and Trademark Office.

TECHNICAL FIELD

The present disclosure generally relates to the administration of medication by infusion and, more particularly, to a check valve.

BACKGROUND

A bag, bottle, syringe, or other container that contains infusion medication or solution is hung from a rack to administer the infusion solution. A tube is connected between the container and an infusion pumping system. A catheter at the end of the tube is inserted into a patient for an intravenous (IV) infusion. The tube may be part of an assembly that includes fittings, connectors, check valves, and pumping elements and is frequently referred to as an "IV set." The infusion solution is administered to the patient when the infusion pumping system is started.

Existing IV check valves include chambers that include inlet ports disposed on the upstream of the IV check valves and outlet ports disposed on the downstream of the IV check valves. The inlet ports allow the fluid to flow from the tube into the check valves, and the outlet ports allow the fluid to flow out of the check valves into the tube. A post may be disposed in the center of the outlet port opening. The post holds a disk against the seat of the inlet port.

IV check valves are normally closed when there is no movement of fluid (e.g., infusion solution) through the IV set. For example, when there is no movement of fluid, the disk in the chamber sits against the seat of the inlet port so that the check valve is sealed. When the fluid flows through the IV set, IV check valves open and allow the fluid to flow from one end of the IV check valve to the other end. For example, when the fluid flows through the IV set, the flow pressure from the fluid movement deflects the disk and creates a gap between the disk and the seat of the inlet port allowing the fluid to flow through the check valve.

The gap between the disk and the seat of the inlet port may be proportional to the flow rate of the fluid. For example, when the flow rate of the fluid decreases (e.g., a low flow condition), the gap between the disk and the seat of the inlet port decreases. A small gap is susceptible to lodging grit between the disk and the seat of the inlet port. When reverse flow is applied while the grit is lodged, the gap between the disk and the seat of the inlet port does not fully close and creates a small leak which renders the valve to be useless.

SUMMARY

IV check valves are normally closed when there is no movement of fluid (e.g., infusion solution) through the IV set. For example, when there is no movement of fluid, the check valve is closed and does not allow fluid to pass the inlet port. When the fluid flows through the IV set, IV check valves open and allow the fluid to flow from one end of the IV check valve to the other end. However, many valves are susceptible to lodging grit and particulates. When reverse flow is applied while the grit is lodged, the inlet port does not fully seal and creates a small leak which renders the valve to be useless.

Providing an IV check valve that prevents grit lodging that leads to leaks and backflows of the fluid would be advantageous. Providing an infusion pump that accomplishes this while also being more reliable, less expensive, and/or quieter than current infusion pumps would be an additional advantage. Described herein are dual check valves that achieve these desired functions and objectives.

A dual check valve includes an upper housing, an intermediate housing, and a lower housing. The upper housing defines an inlet port of the check valve, and includes a first valve seat. The intermediate housing is coupled to the upper housing to define a first cavity, and includes a second valve seat. The lower housing defines an outlet of the check valve, and is coupled to the intermediate housing to define a second cavity. The dual check valve further includes a first disk mounted in the first cavity and configured to selectively contact the first valve seat, and a second disk mounted in the second cavity and configured to selectively contact the second valve seat. When the dual check valve is in an open state, the first disk deflects away from the first valve seat to create a first gap between an upper surface of the first disk and the first valve seat, and the second disk deflects away from the second valve seat to create a second gap between an upper surface of the second disk and the second valve seat. The first gap is smaller than the second gap.

A dual check valve system includes a housing having an upper section including a first radial protrusion, an intermediate section including a second radial protrusion, and a lower section. The upper and intermediate sections define a first cavity. The intermediate and lower sections define a second cavity. The dual check valve system further includes a first check valve and a second check valve. The first check valve includes a first disk configured to engage the first radial protrusion and a second radial protrusion. The second check valve includes a second disk configured to engage the first radial protrusion. A diameter of the first radial protrusion is larger than a diameter of the second radial protrusion.

A dual check valve includes an upper housing, an intermediate housing, and a lower housing. The upper housing defines an inlet of the check valve, and includes a first radial protrusion. The intermediate housing is coupled to the upper housing and defines a first outlet of the check valve. The lower housing is coupled to the intermediate housing, and defines a second outlet of the check valve. The dual check valve further includes a first cavity, a second cavity, a first disk mounted in the first cavity, and a second disk mounted in the second cavity. The first cavity is interposed between and defined by the upper and intermediate housings for fluidly connecting the inlet and the first outlet. The second cavity is interposed between and defined by the intermediate and lower housings for fluidly connecting the first and second outlets. The first disk selectively permits fluid flow in a first direction, and prevents fluid backflow in a second direction opposite to the first direction. The second disk selectively permits fluid flow in the first direction, and prevents fluid backflow in the second direction opposite to the first direction. When a pressure is applied to place the dual check valve in an open state, a stroke of the second disk is greater than a stroke of the first disk.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

The disclosed embodiments of an IV check valves provide a reliable method of delivering a fluid preventing backflow of the fluid.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

The method and system disclosed herein are presented in terms of an infusion pump for the delivery of medical fluid to a patient. It will be apparent to those of ordinary skill in the art that the disclosed concepts may be applied to a variety of mechanisms utilizing check valves.

Figure 1:
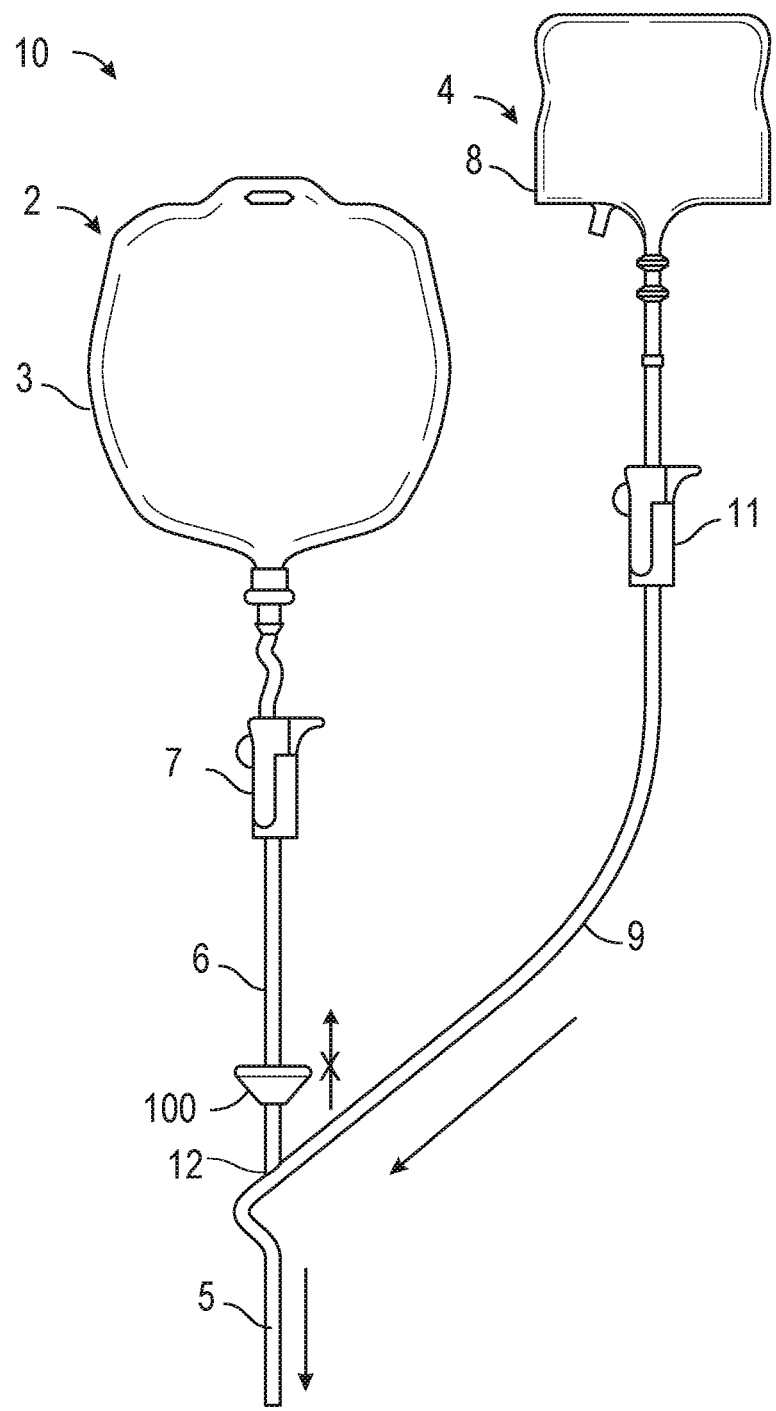
FIG. 1 depicts a perspective view of an IV set having a dual IV check valve according to certain aspects of the disclosure.

FIG. 1 depicts a perspective view of an IV set 10 having a dual check valve 100 according to certain aspects of the disclosure. As illustrated in FIG. 1, an IV set 10 includes the check valve 100 therein. The IV set 10 preferably includes a main fluid system 2 and an auxiliary fluid system 4. An IV pump (not shown) receives fluid from main fluid system 2 and branch or auxiliary fluid system 4 via a supply line 5 and controls and dispenses the fluids therefrom to a patient.

Main fluid system 2 preferably includes a main fluid source such as a fluid bag 3 which may include or contain saline solution or other fluid to be administered to the patient. As illustrated, tube 6 carries flow from a drip chamber 7 to a Y-connector 12. Dual check valve 100 is disposed in tube 6 upstream from the Y-connector 12 and enables flow from fluid bag 3 to the IV pump (not illustrated) while preventing reverse flow (backflow) of fluid from auxiliary fluid system 4 toward fluid bag 3.

Auxiliary fluid system 4 includes an auxiliary fluid source such as a fluid bag 8 which may contain drugs or other fluid to be supplied to the patient for treatment. An auxiliary fluid line 9 carries flow from drip chamber 11 to the Y-connector 12.

Figure 2:
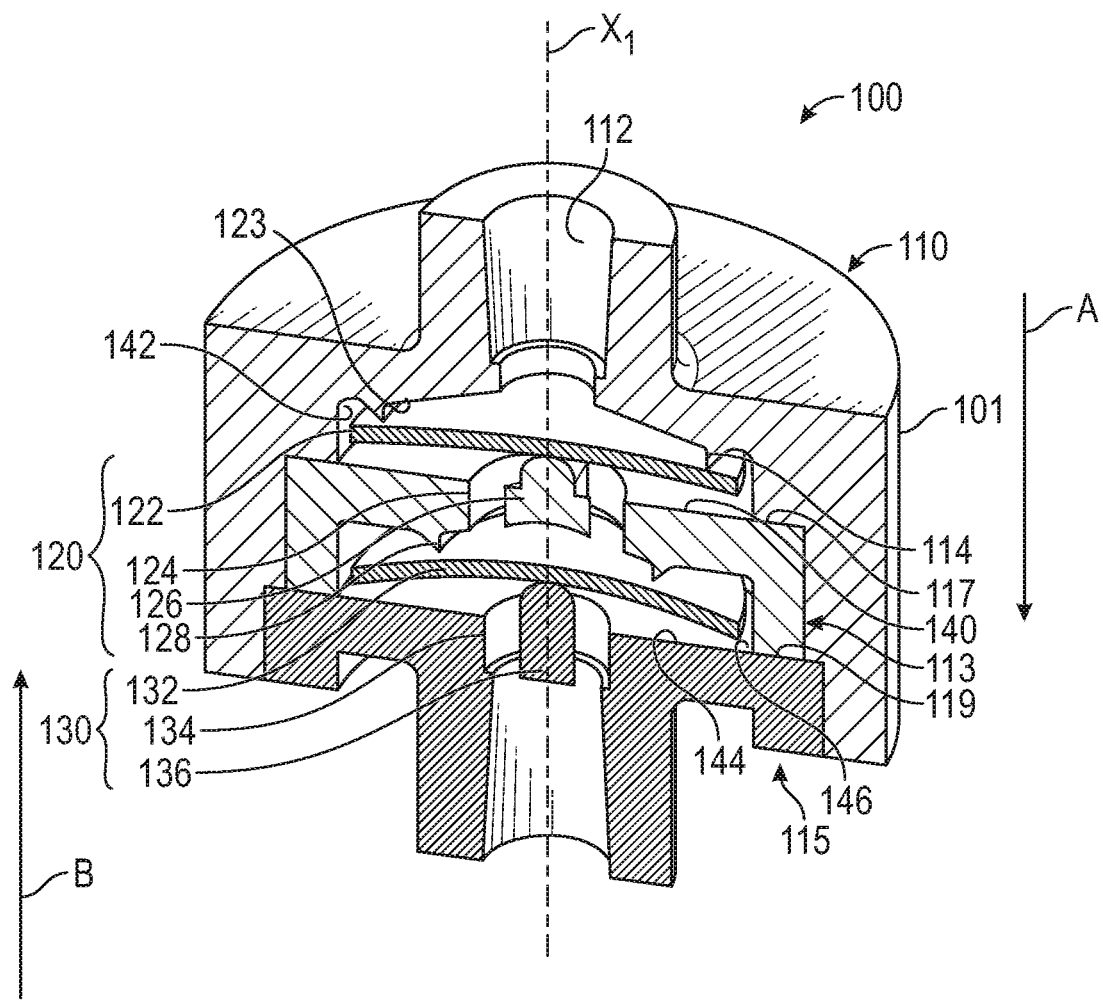
FIG. 2 depicts an exploded view of a dual IV check valve, according to certain aspects of the disclosure.

Various embodiments of the present disclosure relate to a dual check valve that prevents backflow of fluid (e.g., infusion medication or solution). FIG. 2 is an exploded view of a dual check valve 100, in accordance with some embodiments of the present disclosure. Referring to FIG. 1, the dual check valve 100 includes an axially extending body 101 defining a central longitudinal axis X1. The body 101 may be a generally cylindrical (or tubular) structure and may include an upper housing 110, an intermediate housing 113, and a lower housing 115. The upper housing 110 may include a step portion 117. The intermediate housing 113 may include an upstream internal surface 140 and a downstream end surface 119. The step portion 117 and the upstream internal surface 140 of the intermediate housing 113 may axially contact each other to co-operatively form a cavity 142 for housing the first disk 122. The lower housing 115 may also include an upstream internal surface 144, and the end surface 119 of the intermediate housing 113 and the upstream internal surface 144 of the lower housing 115 may axially contact each other to co-operatively form a cavity 146 for housing the second disk 132.

Figure 3:
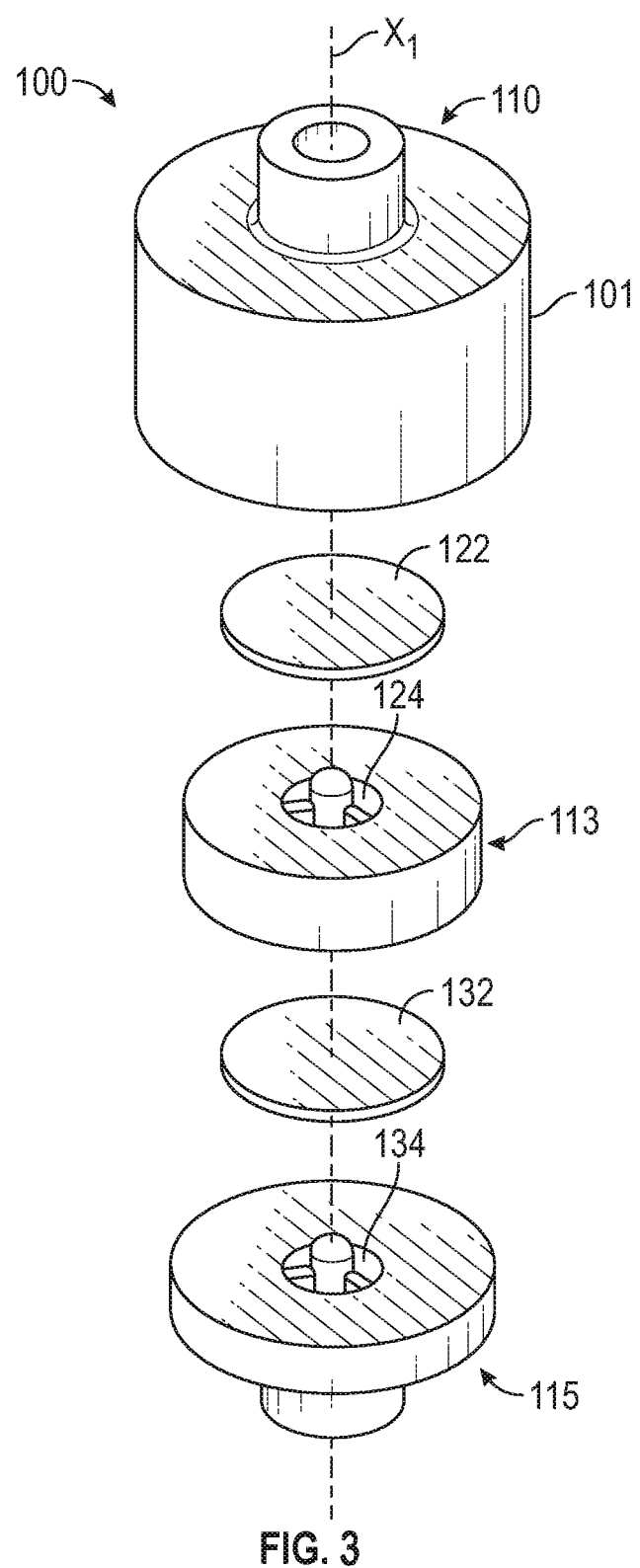
FIG. 3 depicts a perspective cross-sectional view of the dual IV check valve, according to certain aspects of the disclosure.
Figure 4:
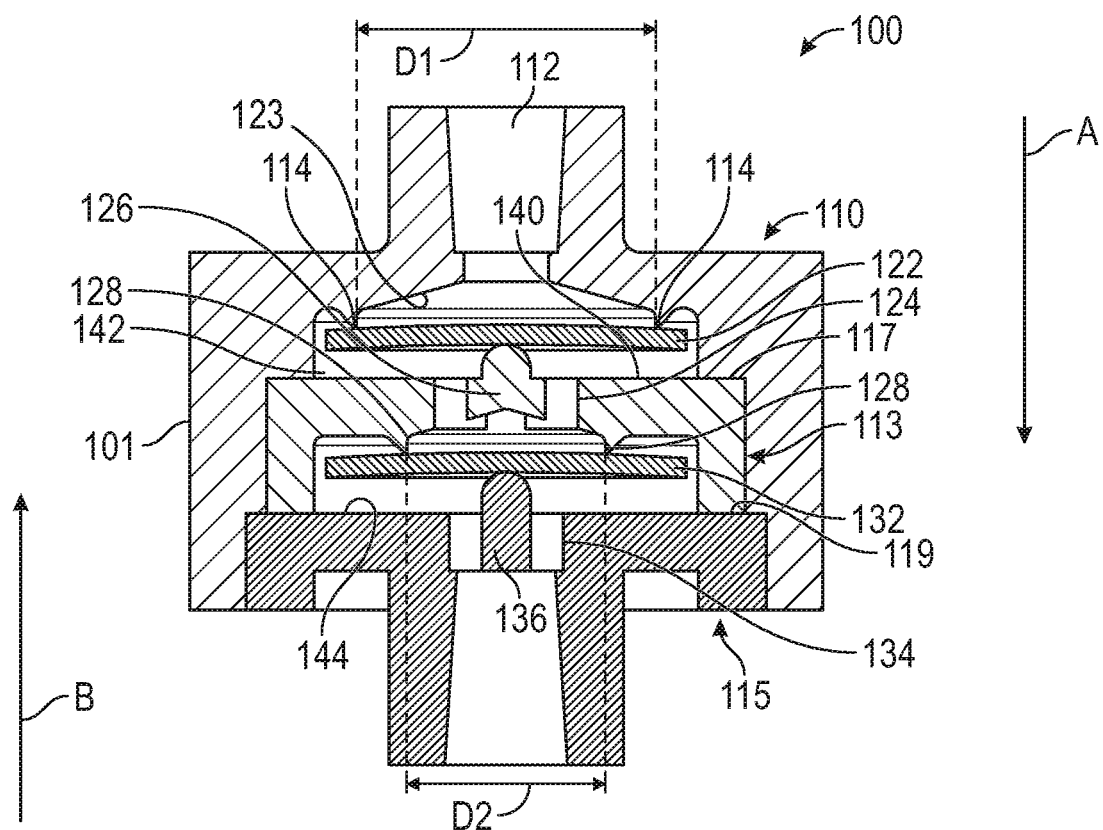
FIG. 4 depicts a cross-sectional view of the dual IV check valve, according to certain aspects of the disclosure.

FIGS. 3 and 4 depict cross-sectional views of the dual check valve 100, according to certain aspects of the disclosure. The dual check valve 100 is displayed in cross-sectional view to more clearly illustrate some of the features of the check valve 100. As depicted, the dual check valve 100 includes a first check valve 120 and a second check valve 130. The first check valve 120 and the second check valve 130 are positioned in line with respect to each other. The first check valve 120 includes a first disk 122 and a first outlet port 124. The second check valve 130 includes a second disk 132 and second outlet port 134.

As illustrated in FIGS. 3 and 4, the upper housing 110 may include an inlet port 112 of the check valve 100 at an upper end thereof, and the lower housing 115 may include the second outlet port 134 of the check valve 100. As is understood, the dual check valve 100 may permit fluid to flow from the inlet port 112 to the second outlet port 134 (as indicated by arrow A), and minimize, or otherwise limit, fluid flow from the second outlet port 134 to the inlet port 112 (as indicated by arrow B). As depicted, the upper housing 110, the intermediate housing 113, and the lower housing 115 may define the cavities 142 and 146 for fluidly connecting the inlet port 112, the first outlet port 124, and the second outlet port 134. In the depicted embodiments, the first disk 122 may be mounted in the cavity 142, and the second disk 132 may be mounted in the cavity 146 to selectively permit fluid flow in a first direction (indicated by arrow A), and prevent fluid backflow (reverse flow) in a second direction opposite to the first direction (indicated by arrow B).

The inlet port 112 of the housing may be connected to the tube 6 of the IV set 10 and allow the fluid to flow from the tube 6 into the dual check valve 100. In operation, the fluid in the dual check valve 100 flows through the first check valve 120 which allows the fluid to move through the first outlet port 124 to the second check valve 130. The fluid flows through the second check valve 130 which allows the fluid to move through the second outlet port 134.

The upper housing 110 may further include a first radial protrusion or valve seat 114 in the inner surface 123 of the upper housing 110. The first radial protrusion 114 surrounds the opening of the inlet port 112. The first radial protrusion 114 extends circularly about the central longitudinal axis X1 of the body 101 and into the cavity 142. In some embodiments, the first radial protrusion 114 defines a sealing surface at a distal end thereof. The first radial protrusion 114 and therefore the sealing surface may be disposed like a ring above the first disk 122. In the normally-closed state of the check valve 100, the first disk 122 contacts the first radial protrusion 114. Because the first disk 122 contacts the first radial protrusion 114, flow of fluid in the reverse direction (illustrated by arrow B), from the first outlet port 124 to the inlet port 112 is prevented.

In some embodiments, the first check valve 120 further includes a second radial protrusion or valve seat 128 extending from a lower surface of the first outlet port 124 that is facing the second check valve 130. The second radial protrusion 128 surrounds the opening of the first outlet port 124. The second radial protrusion 128 extends circularly about the central longitudinal axis X1 of the body 101 and into the cavity 146. In some embodiments, the second radial protrusion 128 defines a sealing surface at a distal end thereof. The second radial protrusion 128 and therefore the sealing surface may be disposed like a ring above the second disk 132. In the normally-closed state of the check valve 100, the second disk 132 contacts the second radial protrusion 128. Because the second disk 132 contacts the second radial protrusion 128, flow of fluid in the reverse direction (illustrated by arrow B), from the second outlet port 134 to the first outlet port 124 is prevented.

In some accordance with some embodiments, as illustrated in FIG. 4, the diameter of the first radial protrusion 114 may be greater than the diameter of the second radial protrusion 128. Thus, when subjected to a pressure from fluid flow, for example an upstream pressure in the direction of arrow A) the stroke of the second disk 132 which seals the second radial protrusion 128 having the smaller diameter will be greater than the stroke of the first disk 122 which seals the first radial protrusion 114 having the larger diameter. Advantageously, the second radial protrusion 128 having a smaller diameter may create a setting in which the second gap is larger than the first gap regardless of the flow rate.

In some aspects, the diameter of the first radial protrusion 114 may be smaller than the diameter of the second radial protrusion 128 so as long as the ratio of the first gap and the second gap is maintained and such that the first gap is smaller than the second gap.

In some aspects, the diameters of the first radial protrusion 114 and the second radial protrusion 128 may be the same. The durometers of the first disk and the second disk may be different from each other in order to maintain functionality equivalent to the first gap being smaller than the second gap. For example, durometer of the first disk may be higher than the durometer of the second disk.

In some other aspects, the durometers of the first disk and the second disk may be the same. However, the thicknesses of the first disk and the second disk may be different from each other. For example, the first disk may be thicker than the second disk so to allow the second disk to deflect more than the first disk. This would maintain functionality of the first disk in relation to the second disk. For example, if the first disk were thicker than the second disk, the first disk would deflect less than the second disk, and passage clearance between the first disk and the first radial protrusion 114 would be less than that of the second disk and the second radial protrusion 128. Accordingly, the first disk would still provide a filter function for the second disk.

Figure 5:
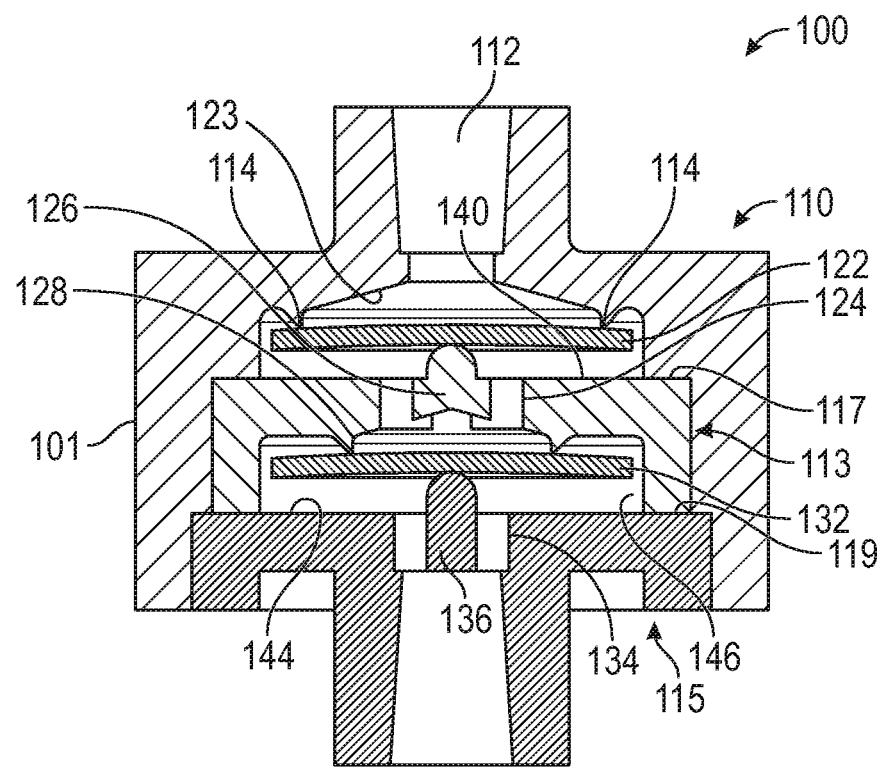
FIG. 5 depicts a cross-sectional view of a dual IV check valve in closed state, according to certain aspects of the disclosure.
Figure 6:
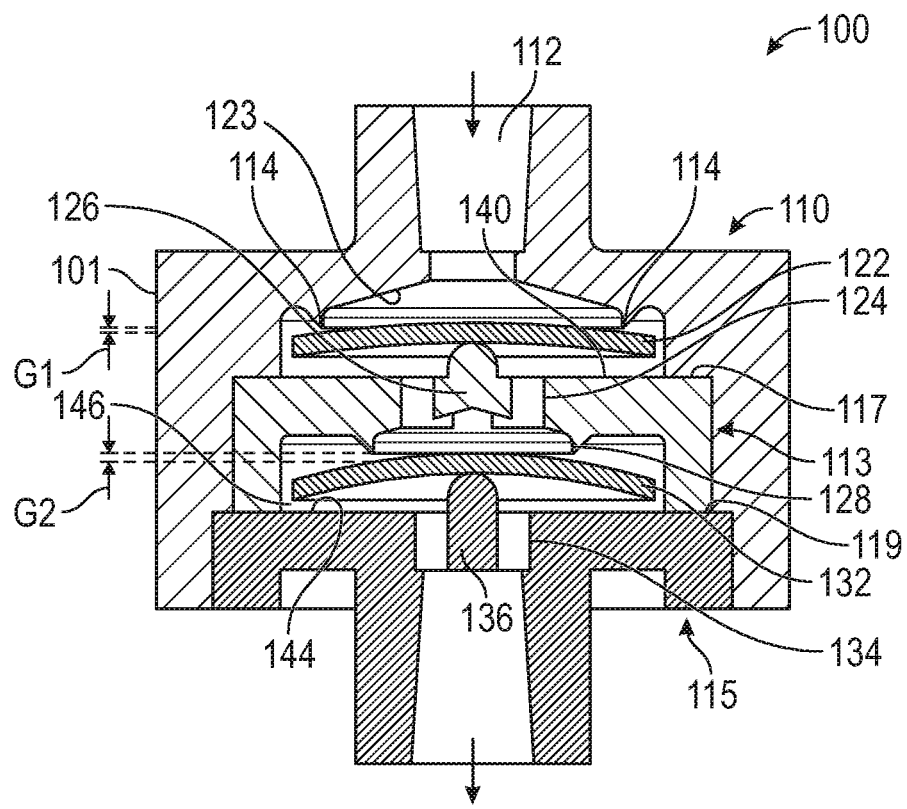
FIG. 6 depicts a cross-sectional view of a dual IV check valve in an opens state, according to certain aspects of the disclosure.

FIG. 5 depicts a cross-sectional view of a dual IV check valve in closed state, according to certain aspects of the disclosure. FIG. 6 depicts a cross-sectional view of a dual IV check valve in an opens state, according to certain aspects of the disclosure. As illustrated in FIGS. 5 and 6, the first disk 122 of the first check valve 120 may be supported by a first post 126 disposed in the center of the first outlet port 124. Similarly, the second disk 132 of the second check valve 130 may be supported by a second post 136 disposed in the center of the second outlet port 134. When equal pressure is applied on both sides of the first disk 122 (e.g., no fluid movement), the first check valve 120 remains in the closed state illustrated in FIG. 5. For example, when the first check valve 120 is in the closed state, a first surface of the first disk 122 that is facing the inlet port 112 is in contact with the first radial protrusion 114. When the pressure applied to an upper surface of the first disk 122 is greater than the pressure applied to a lower surface of the first disk 122 that faces the first outlet port 124 (e.g., fluid flowing from the inlet port to the first outlet port), the first disk 122 deflects towards the first outlet port 124 to move the first disk from the closed state to the open state illustrated in FIG. 6. When the first disk is moved to the open state, a first gap G1 is created between the first disk 122 and the first radial protrusion 114 and allows the fluid to flow through the first gap G1 between the first surface of the first disk 122 and the first radial protrusion 114 (illustrated in FIG. 6).

Similarly, when equal pressure is applied on both sides of the second disk 132 (e.g., no fluid movement), the second check valve 130 remains in the closed state (illustrated in FIG. 5). For example, when the second check valve 130 is in the closed state, a first surface of the second disk 132 that is facing the first check valve 120 is in contact with the second radial protrusion 128. When the pressure applied to the first surface of the second disk 132 is greater than the pressure applied to a second surface of the second disk 132 that is facing the second outlet port 134 (e.g., fluid flowing from the inlet port to the second outlet port), the second disk 132 deflects towards the second outlet port 134 creating a second gap G2 between the second disk 132 and the second radial protrusion 128 and allows the fluid to flow through the second gap G2 between the first surface of the second disk 132 and the second radial protrusion 128 (illustrated in FIG. 6).

During operation, when a downstream pressure (i.e., a pressure applied by a fluid flowing from the first outlet port 124 to the inlet port 112, indicated by arrow B) is applied to the first disk 122, the first disk 122 may deflect towards the first radial protrusion 114 to block the fluid communication between the inlet port 112 and the first outlet port 124, thereby restricting backflow of the fluid from the first outlet port 124 to the inlet port 112. Similarly, when a downstream pressure (i.e., a pressure applied by a fluid flowing from the second outlet port 134 to the first outlet port 124, indicated by arrow B) is applied to the second disk 132, the second disk 132 may deflect towards the second radial protrusion 128 to block the fluid communication between the first outlet port 124 and the second outlet port 134, thereby restricting backflow of the fluid from the first outlet port 124 to the inlet port 112. Preventing backflow of the fluid is advantageous in that it restricts undesirable particulate matter, for example, contained in a drug dispensed from a secondary path from flowing back through the dual check valve 100, thereby preventing the patient from receiving the proper drug dosage concentration or from timely delivery of the drug.

In accordance with some embodiments, the first gap G1 between the first radial protrusion 114 and the first disk 122 is set smaller than the second gap G2 between the second radial protrusion 128 and the second disk 132. For example, as depicted in FIG. 6, the first gap G1 may be 0.005 inches, and the second gap G2 may be 0.008 inches which is greater than the first gap G1. The first gap G1 may act like a filter and allow particles (e.g., grit) no larger than the first gap G1 (e.g., 0.005 inches) to travel past the first disk 122. Accordingly, the particles that have passed through the first gap G1 will not become caught in the second gap G2 (which is larger than the maximum 0.005 inches particle size), and will allow the second check 130 valve to seal when the second check valve 130 moves into the closed position, even when grit is lodged in the first gap G1 and the first check valve 120 does not fully seal. Advantageously, since the size of the particles arriving at the second disk 132 are always smaller than the gap G2, no particles will be lodged or stuck between the second radial protrusion 128 and the upper surface of the second disk 132. The aforementioned configuration is advantageous because when subjected to a downstream pressure sufficient to cause the second disk 132 to deflect upwards, the second valve 130 will fully close, thereby acting as a back-up valve to the first disk 122 if particles get lodged therein and prevent the first disk from fully closing or sealing.

In accordance with some embodiments, the first and second disks 122, 132 may have a generally circular disc shape corresponding to the generally cylindrical shape of the body 101 of the check valve. However, the various embodiments of the present disclosure are not limited to the aforementioned configuration. In some embodiments, the first and second disks 122, 132 may have a non-circular shape, such as square, rectangular, polygonal, or any other shape capable of spanning an area sufficient to cover and overlap the respective first and second radial protrusions 114, 128.

In some embodiments, the first and second disks 122, 132 are not limited to any particular shape or size. In the depicted embodiments, however, the size of the first and second disks 122, 132 may be limited based on desired deflection/bending characteristics of the first and second disks 122, 132 when subjected to either of the upstream or downstream forces. For example, the first and second disks 122, 132 may be sized and shaped so as to flex or bend under fluid pressure to permit forward flow of the fluid into the respective cavities 142, 146, and to limit fluid flow in the reverse direction.

The previous description is provided to enable a person of ordinary skill in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Sonic of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A dual check valve, comprising:
    an upper housing defining an inlet port of the check valve, and including a first valve seat having a first diameter;
    an intermediate housing coupled to the upper housing to define a first cavity, and including a second valve seat having a second diameter, wherein the first diameter is larger than the second diameter;

a lower housing defining an outlet of the check valve, and coupled to the intermediate housing to define a second cavity;
a first disk mounted in the first cavity and configured to selectively contact the first valve seat; and
a second disk mounted in the second cavity and configured to selectively contact the second valve seat,
wherein when the dual check valve is in an open state, the first disk deflects away from the first valve seat to create a first gap between an upper surface of the first disk and the first valve seat, and the second disk deflects away from the second valve seat to create a second gap between an upper surface of the second disk and the second valve seat, the first gap being smaller than the second gap.

2. The dual check valve of claim 1, wherein:
the first valve seat surrounds an opening of the inlet port in the first cavity; and
the second valve seat surrounds an opening of an outlet port defined in the intermediate housing.

3. The dual check valve of claim 1, wherein a thickness of the first disk is equal to or greater than a thickness of the second disk.

4. The dual check valve of claim 1, wherein a diameter of the first disk is equal to or greater than a diameter of the second disk.

5. The dual check valve of claim 1, wherein a diameter of the first disk is less than a diameter of the second disk.

6. The dual check valve of claim 1, wherein a durometer value of the first disk differs from a durometer value of the second disk.

7. The dual check valve of claim 1, wherein when (1) a first pressure applied to the upper surface of the first disk is equal to or less than a second pressure applied to a lower surface of the first disk, and (2) a third pressure applied to the upper surface of the second disk is equal to or less than a fourth pressure applied to a lower surface of the second disk, the dual check valve is in a closed state.

8. The dual check valve of claim 1, wherein when (1) a first pressure applied to the upper surface of the first disk is greater than a second pressure applied to a lower surface of the first disk and (2) a third pressure applied to the upper surface of the second disk is greater than a fourth pressure applied to a lower surface of the second disk, the dual check valve is in the open state.

9. The dual check valve of claim 1, wherein each of the first and second valves comprise an outer perimeter, and wherein the entire perimeter of the first valve is moveable relative to the upper housing, and the entire perimeter of the second valve is moveable relative to the intermediate housing.

10. A dual check valve system, comprising:
a housing comprising an upper section including a first radial protrusion, an intermediate section including a second radial protrusion, and a lower section, wherein:
the upper and intermediate sections define a first cavity; and
the intermediate and lower sections define a second cavity;
a first check valve comprising a first disk configured to engage the first radial protrusion and a second radial protrusion; and
a second check valve comprising a second disk configured to engage the first radial protrusion,
wherein a diameter of the first radial protrusion is larger than a diameter of the second radial protrusion.

11. The dual check valve system of claim 10, wherein:
when a first pressure is applied to the first disk, the first disk is disengaged from the first radial protrusion and a first gap is created between the first disk and the first radial protrusion; and
when a second pressure is applied to the second disk, the second disk is disengaged from the second radial protrusion and a second gap is created between the second disk and the second protrusion, the first gap being smaller than the second gap.

12. The dual check valve system of claim 11, wherein:
the first check valve further comprises a first outlet port and a first post, the first disk being supported by the first post to engage the first radial protrusion; and
the second check valve further comprises a second outlet port and second post, the second disk being supported by the second post to engage the second radial protrusion.

13. The dual check valve system of claim 12, wherein a top surface of the first disk engages the first protrusion, and a bottom surface of the first disk is in contact with a tip of the first post, and
wherein a top surface of the second disk engages the second protrusion, and a bottom surface of the second disk is in contact with a tip of the second post.

14. The dual check valve system of claim 12, wherein the first post supports the first disk a diameter of the first radial protrusion is equal or larger than a diameter of the second radial protrusion.

15. The dual check valve system of claim 10, wherein a thickness of the first disk is equal to or greater than a thickness of the second disk.

16. The dual check valve of claim 10, wherein a diameter of the first disk is equal to or greater than a diameter of the second disk.

17. The dual check valve system of claim 10, wherein a diameter of the first disk is less than a diameter of the second disk.

18. The dual check valve system of claim 10, wherein a durometer value of the first disk differs from a durometer value of the second disk.

19. A dual check valve, comprising:
an upper housing defining an inlet of the check valve, and including a first radial protrusion;
an intermediate housing coupled to the upper housing, and including a second radial protrusion, the intermediate housing defining a first outlet of the check valve;
a lower housing coupled to the intermediate housing, and defining a second outlet of the check valve,
a first cavity interposed between and defined by the upper and intermediate housings for fluidly connecting the inlet and the first outlet;
a second cavity interposed between and defined by the intermediate and lower housings for fluidly connecting the first and second outlets;
a first disk mounted in the first cavity to selectively permit fluid flow in a first direction, and prevent fluid backflow in a second direction opposite to the first direction; and
a second disk mounted in the second cavity to selectively permit fluid flow in the first direction, and prevent fluid backflow in the second direction opposite to the first direction, wherein a thickness of the first disk is greater than a thickness of the second disk, such that the second disk is more flexible than the first disk;
wherein when a pressure is applied to place the dual check valve in an open state, a stroke length between the second radial protrusion and the top surface of the second disk is greater than a stroke length between the first radial protrusion and the top surface of the first disk.

20. The dual check valve of claim 19, wherein a diameter of the first radial protrusion is equal to or larger than a diameter of the second radial protrusion.

* * * * *